(12) United States Patent
Kreitzer

(10) Patent No.: US 6,834,614 B1
(45) Date of Patent: Dec. 28, 2004

(54) METHOD AND APPARATUS FOR ENCAPSULATING, IMPLANTING, AND REDUCING THE MORTALITY RATE IN EARTHWORM COCOONS

(76) Inventor: William R. Kreitzer, 1011 N. Church St., Gibson City, IL (US) 60936

( * ) Notice: Subject to any disclaimer, the term of this patent is extended or adjusted under 35 U.S.C. 154(b) by 0 days.

(21) Appl. No.: 10/787,795

(22) Filed: Feb. 26, 2004

(51) Int. Cl.[7] .......................... A01K 67/033; A01C 1/00
(52) U.S. Cl. ......................................... 119/6.7; 111/200
(58) Field of Search ............................ 119/6.7; 47/57.6; 111/200, 900

(56) References Cited

U.S. PATENT DOCUMENTS 4,143,161 A * 3/1979 Ciulla ............................ 426/1
5,127,186 A * 7/1992 Kreitzer ...................... 47/57.6
5,250,082 A * 10/1993 Teng et al. ................... 47/57.6

* cited by examiner

Primary Examiner—Robert P. Swiatek
(74) Attorney, Agent, or Firm—Tod R. Nissle, P.C.

(57) ABSTRACT

A improved method and apparatus is provided for encapsulating earthworm cocoons. The method and apparatus coat the cocoons with a Histosol soil to produce an encapsulated cocoon having a size and weight comparable to that of a selected crop seed. The method and apparatus of the invention decrease the mortality of earthworm eggs and help prevent the separation of encapsulated cocoons from crop seed after the cocoons are admixed therewith.

3 Claims, 1 Drawing Sheet

Figure 1:
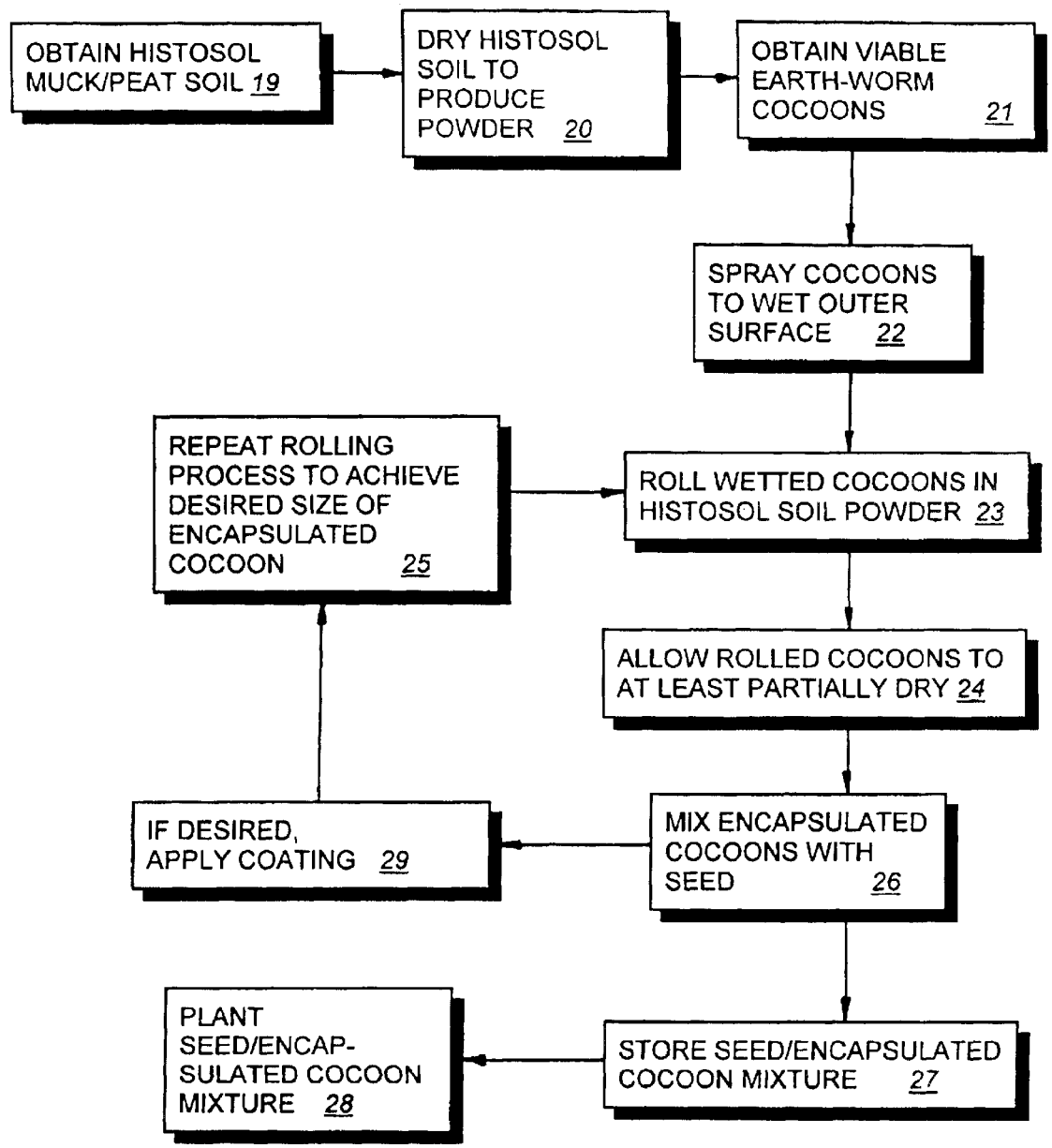

METHOD AND APPARATUS FOR ENCAPSULATING, IMPLANTING, AND REDUCING THE MORTALITY RATE IN EARTHWORM COCOONS

This invention pertains to earthworms.

More particularly, the invention pertains to a method and apparatus for encapsulating earthworm cocoons that reduces the mortality rate of the worm eggs in the cocoons.

In another respect, the invention pertain to a method and apparatus for encapsulating earthworm cocoons that facilitates both the integration of encapsulated cocoons with seeds and the implanting in the ground of the encapsulated cocoons.

In U.S. Pat. No. 5,127,186, a system is described for encapsulating and implanting earthworm cocoons. The system encapsulates earthworm cocoons in gel capsules along with a supplemental material that gives the capsule a density approximately equal to that of the seed being planted. Since earthworm cocoons are lighter in weight than many common seed crops, the supplemental material added to the gel capsule is typically relatively dense and can comprise, for example, seeds, pesticides, fertilizers, energy sources, growth promoters, growth regulators, microorganisms, propylene glycol, sodium alginate, guar gum, and gels. Such supplemental materials also function to protect the cocoon. The encapsulation system in U.S. Pat. No. 5,127,186 does, however, have particular disadvantages.

First, obtaining gel capsules of a size comparable to that of corn or soybean is practical. Obtaining gel capsules of a size comparable to that of smaller seeds is difficult, if not impossible.

Second, even if a small gel capsule is obtained, fitting both the earthworm cocoon and the supplemental material in the capsule can be impractical.

Third, gel capsules usually have a smooth outer surface that promotes undesirably separation of the gel capsules from seed that is intermixed with the gel capsules.

Fourth, it now appears that it is not the combination of size and density that is critical in intermixing encapsulated cocoons with seeds, it is the combination of size and weight.

Accordingly, it would be highly desirable to provide an improved earthworm cocoon encapsulating method and apparatus that could be readily adapted to produce different sized encapsulated cocoons, that would not require the intermixing of a supplemental material and an earthworm cocoon, that would not require cocoons and supplemental material to be loaded into a capsule, that would retard the separation from seed of the encapsulated cocoons, and that would permit ready alteration of the weight and size of encapsulated cocoons.

Therefore, it is a principal object of the invention to provide an improved method and apparatus for encapsulating earthworm cocoons.

Another object of the invention is to provide encapsulated earthworm cocoons that are shaped and dimensioned and textured to retard separation of the encapsulated cocoons from seed intermixed with the encapsulated cocoons.

A further object of the invention is to provide an improved earthworm cocoon encapsulation method that facilitates the production of encapsulated cocoons having varying sizes, weights, and textures.

Still another object of the invention is to provide an improved earthworm cocoon encapsulation method that prolongs the period of time the encapsulated cocoons can be stored with viable eggs prior to being buried in the ground to hatch the eggs.

These and other, further and more specific objects and advantages of the invention will be apparent to those skilled in the art from the following detailed description thereof, taken in conjunction with the drawings, in which FIG. 1 is a block flow diagram illustrating the cocoon encapsulating method of the invention.

Briefly, in accordance with the invention, I provide an improved method for encapsulating an earthworm cocoon. The method includes the steps of obtaining a histosol soil; drying the soil to form a histosol soil powder; moistening the earthworm cocoon; rolling the moistened earthworm cocoon at least once in the histosol soil powder to produce an encapsulated cocoon coated at least in part by histosol soil powder.

In another embodiment of the invention, I provide an improved system for planting simultaneously in a field crop seed and a plurality of earthworm cocoons. The system includes the steps of encapsulating each of the plurality of earthworm cocoons separately in a coating including soil to form soil encapsulated cocoons. The coating has an irregularly shaped surface. The method also includes the steps of admixing the encapsulated cocoons with crop seed; and, planting simultaneously the crop seed and the admixed encapsulated cocoons.

In a further embodiment of the invention, I provide an improved system for planting simultaneously in a field crop seed and a plurality of earthworm cocoons. The system includes the steps of encapsulating each of the plurality of earthworm cocoons separately in a coating including soil to form soil encapsulated cocoons. Each of the soil encapsulated cocoons has substantially the same size and weight as one of the crop seed. The method also includes the steps of admixing the encapsulated cocoons with crop seed; and, planting simultaneously the crop seed and the admixed encapsulated cocoons.

Turning now to the drawings, which depict the presently preferred embodiments of the invention for the purpose of illustrating the practice thereof and not by way of limitation of the scope of the invention and in which like reference characters refer to corresponding elements throughout the several views, FIG. 1 is a block diagram illustrating a cocoon encapsulation system in accordance with one embodiment of the invention.

As used herein, the size of a crop seed or of an encapsulated cocoon is defined as its greatest width, and term soil refers to the solid components (minerals, plant parts etc.) of a particular soil order and not to moisture normally found in the soil order. The twelve soil orders are Alfisols, Entisols, Inceptisols, Mollisols, Spodosols, Histosols, Ultisols, Andisols, Aridisols, Oxisole, Vertisols, and Gelisols.

The Histosol soil order includes most of the worlds' organic soils. A soil typically is classified as a Histosol soil when at least half of the upper eighty centimeters of the soil is highly organic. If the soil is a shallow soil, it is a Histosol if organic material of any thickness is above bedrock or is within material that contains voids filled with organic materials. The soil order Histosol includes the suborders Folists, Fibrists, Hemists, and Saprists.

Folists are organic soils that formed under non-flooded conditions. Such soils include leaf litter and decaying wood fragment that gather on bedrock.

Fibrists, Hemists, and Saprists form under flooded conditions. Of these three suborders, Fibrists evidence the least amount of decay and typically include three-fourths or more by volume of fibers that are captured on a 100 mesh screen. Hemists have a decomposition that is intermediate the less decomposed Fibrists and the Saprists, which are more thoroughly decomposed. Saprists normally are black. Black organic "muck" soils consist of highly decomposed organic materials, and are Saprists. Saprists generally have greater ash content than the other Histosol suborders. Histosols typically have from 0.5 to 4.0% total nitrogen; have from 0.01 to 0.3% phosphorous, most of which is in the organic form and must be mineralized to be utilized by a plant; have from 0.5 to 2.0% potassium; and, have up to 32% by weight silicon. The Histosol silicon content can also be quite low, less than 4%. Histosols can also contain calcium, magnesium, sulfur and other soil nutrients.

While it is possible to use any soil order in the practice of the invention, Histosols are preferred in the practice of the invention; particularly the Saprists because of their mineral content and lower fiber content and because they tend to readily form a coating on earthworm cocoons when moistened.

The Histosol soil used in the practice of the invention is presently dried, and is ground or pulverized to produce a powder. Grinding the soil to a powder is preferred because it facilitates coating earthworm cocoons. The powder can be sprayed or otherwise applied to an earthworm cocoon. The presently preferred method comprises spraying or misting cocoons with water to wet the outer surface of the cocoons and then rolling or tumbling the cocoons in the soil powder to form a powder coating on the cocoon. After the powder is sufficiently dry to form a coating that adheres to the earthworm cocoon, the process can be repeated by misting the coating and again rolling the cocoon in the soil powder. The drying-misting-rolling sequence can be repeated as many times as desired to form a coating on the cocoon having the desired thickness and surface contours.

One advantage of the soil powder coating process is that the coating can have an irregular shape, i.e., does not need to be spherical. The irregular shape tends to make it more difficult for encapsulated cocoons to separate from crop seed after the encapsulated cocoons are admixed with the crop seed.

Another advantage of the soil powder coating is that it normally also is not unusually slick because the particulate that forms the coating has edges and corners. This "non-slick" surface also tends to slow separation of encapsulated cocoons from crop seed. The soil powder coating on earthworm cocoons can be made more nearly spherical, however, by repeatedly applying coatings to the cocoons.

A further advantage of the soil powder coating is that it can, by varying the number of coatings, be readily used to vary the size of the resulting encapsulated earthworm cocoons.

Still another advantage of the soil powder coating is that it readily disintegrates when introduced in the ground.

Still a further advantage of the soil powder coating is that it is gas permeable and permits the passage of oxygen and carbon dioxide.

Yet another advantage of the soil powder coating is that it normally is readily coated with wax or another desired substance.

Yet a further advantage of the soil powder that it can be admixed with a variety of other components prior to being applied to earthworm cocoons. Such components can, by way of example and not limitation, include pesticides, fertilizers, energy sources, growth promoters, growth regulators, microorganisms, minerals, propylene glycol, sodium alginate, guar gum, gel agents, moisture, and colorants.

Yet still a further advantage of the soil powder coating-especially when the soil powder is coated with a composition that retards the evaporation of water-is that it tends to seal moisture in and to retain some moisture around the encapsulated cocoon. It consequently retards the development of the cocoon so K has an extended incubation period. The worm eggs will hatch or survive after a selected period of time. This significant decrease in worm egg mortality is an unexpected, surprising, and advantageous result of the method of the invention.

The Folists and Fibrists tend to be termed "peat" soils because plant parts can be recognized in the soils. Hemists also tend to have some recognizable plant parts. Plant parts tend to make it more difficult to form a soil coating on an earthworm cocoon. ConsequenUy, although Folists and Fibrists or Hemists or other soil orders can be utilized in the practice of the invention, "muck" Saprists are presently preferred. One advantage of utilizing "muck" soils is that they are readily available and do not have to be manufactured. The mineral content of such soils is also useful for supplementing soils into which encapsulated earthworms cocoons are injected, with or without crop seed. In some instances, it likely is beneficial simply to introduce encapsulated earthworm cocoons into a field without introducing crop seeds or other seeds or materials at the same time.

In use, as shown in FIG. 1, a Histosol soil is obtained 19, preferably a much/peat soil, most preferably a muck soil. The soil is dried 20 by exposing the soil to the sun or by using other suitable apparatus to produce a powder, and is also, if desired, ground or pulverized. The average size of each powder particle can vary as desired, but preferably is small enough such that the powder will adhere to a moistened or wetted cocoon when the cocoon is rolled or tumbled in the powder. Viable earthworm cocoons are obtained 21, and are sprayed or misted 22 with suitable apparatus to moisten or otherwise wet the outer surface of the cocoons. The moistened cocoons are rolled 23 in the soil powder in mixing or tumbling or other apparatus to form a soil powder coating that at least partially (preferably completely) covers the cocoons. The rolled cocoons can be permitted to at least partially dry 24. The rolling process is repeated 25 as many times as desired to obtain an encapsulated cocoon having the desired size and/or weight. In some instances the rolling process may not be repeated and only a single coating is formed on the earthworm cocoons. When the encapsulated cocoons are to be admixed with crop seed, the size of the encapsulated cocoon typically is within 10% of the average size of the crop seed, i.e. is between a size that is 10% less than the average size of the crop seed and a size that is 10% greater than the average size of the crop seed. Similarly, the weight of the encapsulated cocoon typically is within 10% to 20% of the average weight of the crop seed. The weight and/or size of the encapsulated cocoon are important in the practice of the invention to minimize the tendency of encapsulated cocoons to cull or separate out from crop seed. The density of the earthworm cocoon and/or soil coating rarely, if ever, will equal that of a crop seed. If the density of the soil coating is equivalent to that of a seed, that equivalence does not insure that the encapsulated cocoon will significantly resist separation from crop seed. If the density of the coating equals that of the crop seed, if the encapsulated cocoon is the same side as a crop seed, and if the total weight of the encapsulated cocoon is, however, too heavy or too light, then the encapsulated cocoon will tend to separate from admixed crop seed.

After the cocoons are moistened and rolled the desired number of times, the encapsulated cocoons are stored by refrigerating the cocoons to retard the development of the embryo and to help slow the evaporation rate of the encapsulation material 27. The rolling of the cocoons typically take place at an ambient temperature in the range of 60 to 80 degree F., or at a temperature that will not injure the viable worm eggs in the cocoons. The drying of the encapsulated cocoons is sufficient for the cocoons to feel dry to the touch, but is not intended to remove all moisture from the soil coating or from the cocoon. In fact, one particular advantage of the soil coating procedure of the invention is, as earlier noted, that successive coatings will tend to seal moisture in earlier coatings on a cocoon and to retard the evaporation of moisture from the earlier coatings and from the cocoon. This retention of moisture and retardation of moisture evaporation is believed important in extending the viability of worm eggs that reside in the encapsulated cocoon. Worm eggs encapsulated in accordance with the method of the invention are, if stored in a cool location at a temperature above freezing, believed to remain viable for at least six months, more likely for at least a year. In many cases, 70% to 80% of the worm eggs hatch when the encapsulated cocoons are then placed in the ground under conditions that reasonably favor hatching of the cocoon worm eggs. The worm eggs typically hatch when there is a reasonable amount of moisture in the ground, when the ground is composed of reasonably fertile loose soil, and when the temperature of the surface of the ground during the day is in the range of 60 degrees to 90 degrees F.

A coating of wax or a supplemental coating of another material can, if desired, be applied to the partially dried soil-encapsulated cocoon to help bind the soil together and to help retain moisture in the encapsulated cocoon. Omitting the wax or other supplemental coating can facilitate the disintegration of the encapsulating soil coating when the cocoons are planted in a field. Omitting a coating may be particularly advantageous if the cocoons are implanted in a field within thirty to sixty days after they are encapsulated.

Encapsulated cocoons can be directly implanted in a field, can be stored and implanted in a field at a later date, can be admixed with a peat or other soil or material and spread on or planted in the ground, or can be admixed with crop seed 26. After the encapsulated cocoons are admixed with crop seed, the encapsulated cocoons can be stored 27 or planted 28.

The following example is presented by way of illustration, and not limitation, of the invention.

EXAMPLE

A clean encapsulating pan or container is provided, along with means to alter the orientation of the pan or container so that the earthworm cocoons can be rolled in the pan or container.

An aqueous solution if provided by admixing VANGEL (TM) or another surfactant with water to produce the aqueous solution. The concentration of the surfactant in the aqueous solution can vary, but typically is in the range of about 1% to 15% by weight of surfactant.

Encapsulating particulate is produced by drying and grinding a Histosol or other soil in the manner earlier described to produce a particulate. The size of the particulate particles can vary as desired, but a fine powder similar in consistency to flour is presently preferred.

Earthworm cocoons are provided and placed in the pan. An airbrush or other mechanism is used to moisten, while the cocoons are rolled in the pan, the earthworm cocoons with the surfactant aqueous solution. If too much of the aqueous solution is applied to the cocoons, the cocoons will stick together. This is to be avoided.

Once the cocoons are moistened, a small amount of the encapsulating particulate is, while the cocoons roll in the pan, sprayed on or otherwise applied to the cocoons. The cocoons are sprayed again with the aqueous surfactant solution to moisten the coating. A small amount of the encapsulating particulate is again sprayed on the cocoons. If too much particulate is applied, the particulate will not stick to the cocoons. Once the earthworm cocoons have a solid layer of powder around them, they are thoroughly wetted by spraying the cocoons with the aqueous surfactant solution. Slightly larger quantities of particulate are sprayed on the encapsulated cocoons. This coating process is repeated as many times as desired. After each particulate coating, the encapsulated cocoons are thoroughly wetted as much as possible with the aqueous surfactant solution before more particulate is applied. Once the desired number of coatings are applied and the desired size and weight is achieved for each encapsulated cocoon, the finished encapsulated cocoons are sprayed with the aqueous surfactant solution to make the encapsulated cocoons as wet as possible. The cocoons are rolled in the pan to smooth the outer surface and to compact the encapsulation particulate.

A wax coating is prepared by admixing PEG 2000 (polyethylene glycol) and a wax such as, for example, GELUCIRE (TM). Any desired wax can be utilized. The PEG and wax are melted and admixed to produce a homogeneous coating composition. The coating composition is applied to the encapsulated cocoons. When the wax contacts the surface of a cocoon, the wax hardens almost instantaneously and adheres to the cocoon. If the wax is too cool when it is sprayed onto the cocoons, the wax does not adhere to the cocoons. After one layer cools, a second layer of wax coating composition can be applied to the encapsulated cocoons. When the second layer cools, a third layer can be applied, and so on. After the final wax layer is applied, the encapsulated cocoons are rolled in a clean pan to smooth the surface of the wax coating. The cocoons are placed in an open container and refrigerated to facilitate hardening of the wax. The encapsulated cocoons are refrigerated overnight and are, if desired, stirred frequently to avoid the concentration of heat in areas of the cocoon that are not open to the air but that contact other cocoons or a side of the container. Such heat concentrations can melt portions of the wax. After being refrigerated overnight, the cocoons are placed in a container for shipping.

Having set forth my invention in terms to enable those skilled in the art to understand the practice the invention and having set forth the presently preferred embodiments and uses thereof, I claim:

1. A method for encapsulating an earthworm cocoon, comprising the steps of:
    (a) obtaining a histosol soil;
    (b) drying said soil to form a histosol soil powder;
    (c) moistening the earthworm cocoon;
    (d) rolling the moistened earthworm cocoon at least once in said histosol soil powder to produce an encapsulated cocoon coated by histosol soil powder; and,
    (e) drying said histosol soil coating.

2. A method for planting simultaneously in a field crop seed and a plurality of earthworm cocoons, comprising the steps of:
    (a) encapsulating each of the plurality of earthworm cocoons separately in a coating including soil to form soil encapsulated cocoons, said coating having an irregularly shaped surface;
    (b) admixing said encapsulated cocoons with crop seed; and, (c) planting simultaneously said crop seed and said admixed encapsulated cocoons.

3. A method for planting simultaneously in a field crop seed and a plurality of earthworm cocoons, comprising the steps of:
(a) encapsulating each of the plurality of earthworm cocoons separately in a coating including soil to form soil encapsulated cocoons, each of said soil encapsulated cocoons having substantially the same size and weight as one of said crop seed;
(b) admixing said encapsulated cocoons with crop seed; and,
(c) planting simultaneously said crop seed and said admixed encapsulated cocoons.

* * * * *